US008013175B2

(12) United States Patent
Aoshima et al.

(10) Patent No.: US 8,013,175 B2
(45) Date of Patent: Sep. 6, 2011

(54) METHOD OF REFINING EPISESAMIN

(75) Inventors: Yukihiro Aoshima, Osaka (JP); Masaaki Nakai, Osaka (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 94 days.

(21) Appl. No.: 12/084,651

(22) PCT Filed: Nov. 1, 2006

(86) PCT No.: PCT/JP2006/321828
§ 371 (c)(1), (2), (4) Date: May 7, 2008

(87) PCT Pub. No.: WO2007/055129
PCT Pub. Date: May 18, 2007

(65) Prior Publication Data
US 2009/0156838 A1 Jun. 18, 2009

(30) Foreign Application Priority Data
Nov. 8, 2005 (JP) .................................. 2005-324045

(51) Int. Cl.
*C07D 307/00* (2006.01)
*C07D 317/00* (2006.01)
*C07D 307/77* (2006.01)
(52) U.S. Cl. .................... 549/448; 549/435; 549/456
(58) Field of Classification Search .................. 549/435, 549/448, 456
See application file for complete search history.

(56) References Cited

U.S. PATENT DOCUMENTS

| 5,211,953 | A | 5/1993 | Shinmen et al. |
| 5,902,458 | A | 5/1999 | Sugiura et al. |
| 5,948,451 | A | 9/1999 | Igarashi |
| 6,033,706 | A * | 3/2000 | Silkeberg et al. ............. 426/417 |

FOREIGN PATENT DOCUMENTS

| EP | 449 436 | 10/1991 |
| JP | 03-231996 | 10/1991 |
| JP | 7 25764 | 3/1995 |
| JP | 10-7676 | 1/1998 |
| JP | 2003-183172 | 7/2003 |
| JP | 2003-192562 | 7/2003 |
| WO | 97/01968 | 1/1997 |

OTHER PUBLICATIONS

Biswanath Das et al., "Clay Catalysed Convenient Isomerization of Natural Furofuran Lignans Under Microwave Irradiation", Synthetic Communications, 2000, pp. 4001-4006, vol. 30, No. 22, Published by Marcel Dekker, Inc.

(Continued)

*Primary Examiner* — Taylor Victor Oh
(74) *Attorney, Agent, or Firm* — Drinker Biddle & Reath LLP

(57) ABSTRACT

There is disclosed an episesamin refining method in which a mixture of sesamin components that contains sesamin, episesamin and the like is brought into contact with an aqueous medium to form a slurried mixture, and thereafter the solids are separated from the mixture or the slurried mixture is dissolved in a suitable aqueous medium under heating and, thereafter, the solution is slowly cooled to recrystallize, thereby yielding an episesamin-enriched composition with an increased relative episesamin content. By the present invention, episesamin can be conveniently and efficiently refined from a mixture of sesamin components that mainly comprises sesamin and episesamin.

12 Claims, 4 Drawing Sheets

OTHER PUBLICATIONS

Y. Fukuda et al., "Contribution of Lignan Analogues to Antioxidative Activity of Refined Unroasted Sesame Seed Oil", J. Am., Oil. Chem. Soc., Aug. 1986, pp. 1027-1031, vol. 63, No. 8.

International Search Report dated Nov. 28, 2006 for PCT/JP2006/321828 filed Nov. 1, 2006.

European Search Report dated Aug. 4, 2009, issued in EP 06822757.8.

Namiki et al., "Goma—Sono Kagaku to Kinousei", Maruzen Planet Co., Ltd. (1998) p. 47, lines 3-4; and p. 51, lines 12-16 (partial translation).

Umeda-Sawada, Rumi et al., The Metabolism and Distribution of Sesame Lignans (sesamin and episesamin) in Rats, LIPIDS, vol. 34, No. 6 (1999), pp. 633-637.

Kushiro, Masayo et al., "Comparative Effect of Sesamin and Episesamin on the Activity and Gene Expression of Enzymes in Fatty Acid Oxidation and Synthesis in Rat Liver", Journal of Nutritional Biochemistry 13 (2002) pp. 289-295.

International Preliminary Report on Patentability dated May 14, 2008, issued in PCT/JP2006/321828 filed Nov. 1, 2006.

* cited by examiner

[FIG. 1]
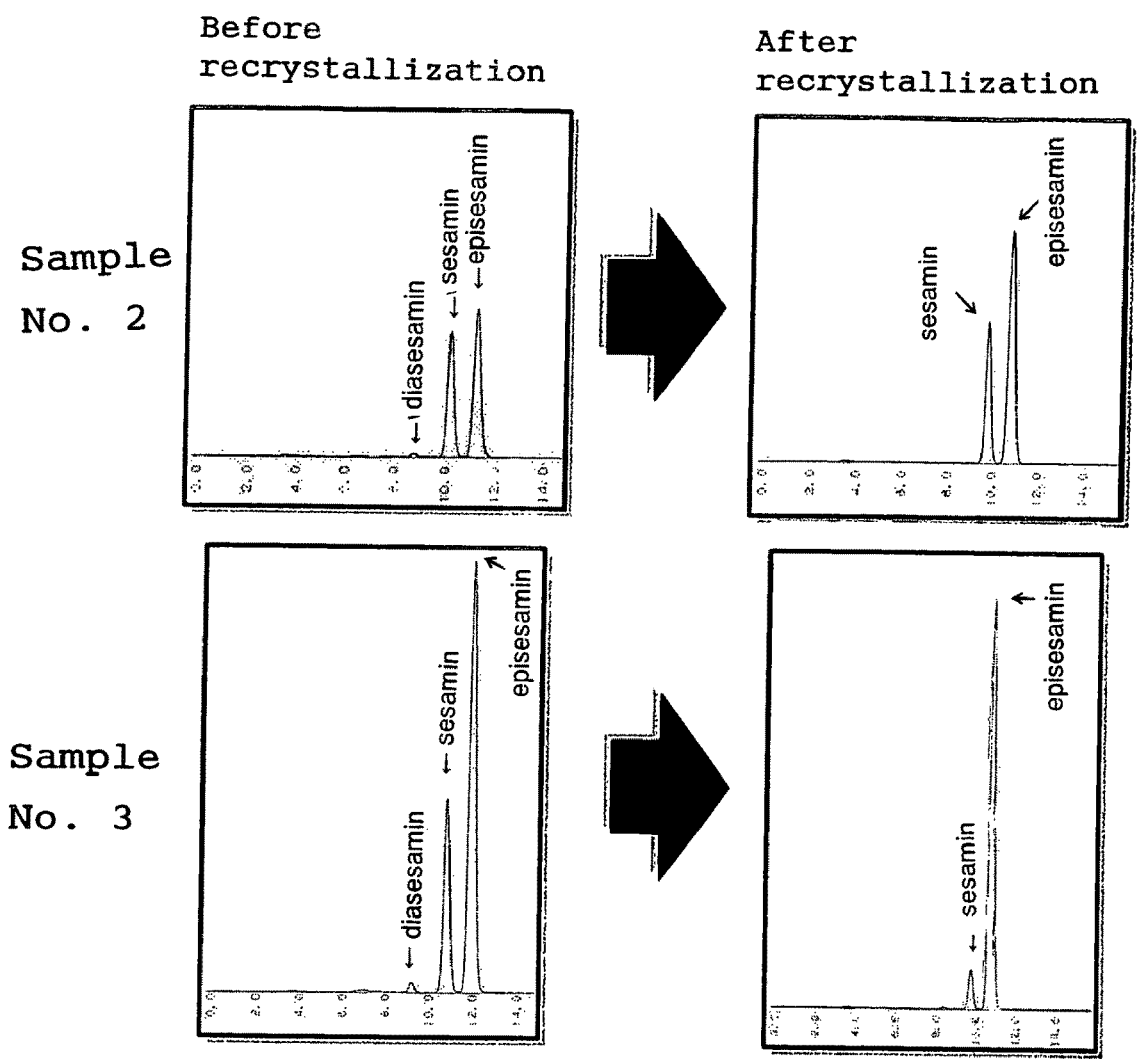

[FIG. 2]
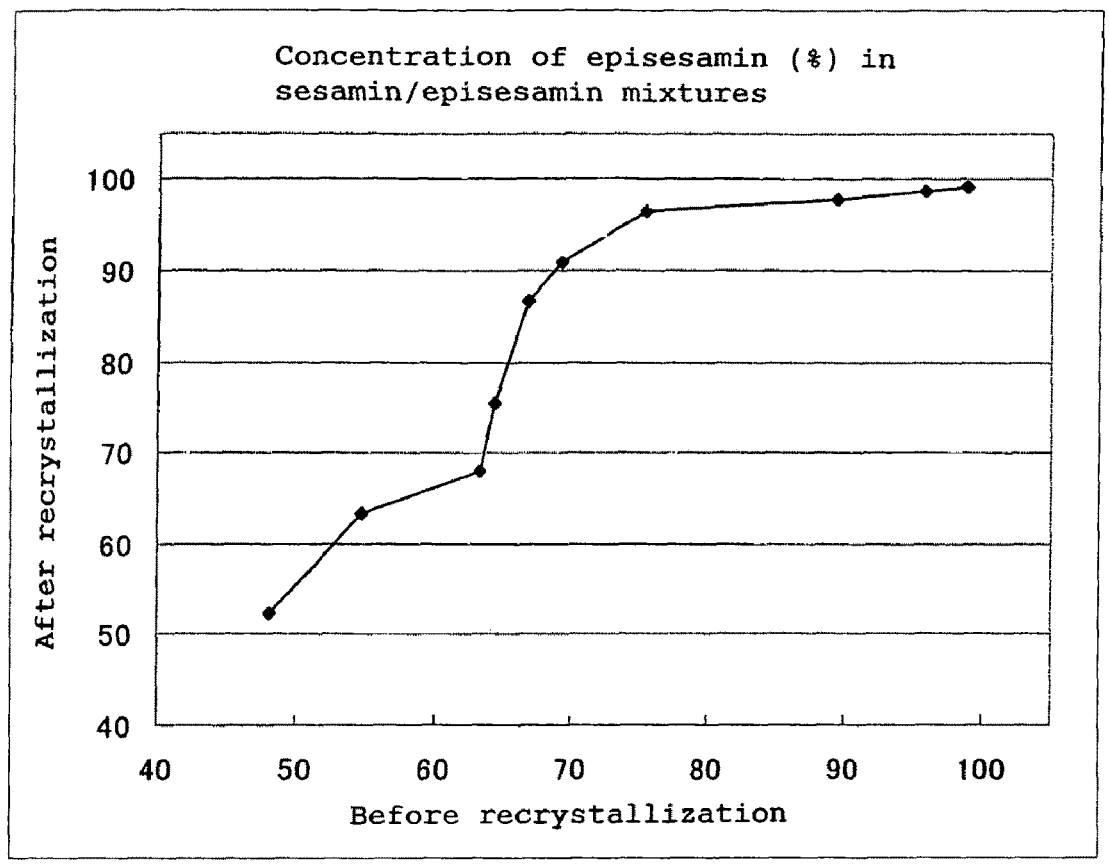

[FIG. 3]
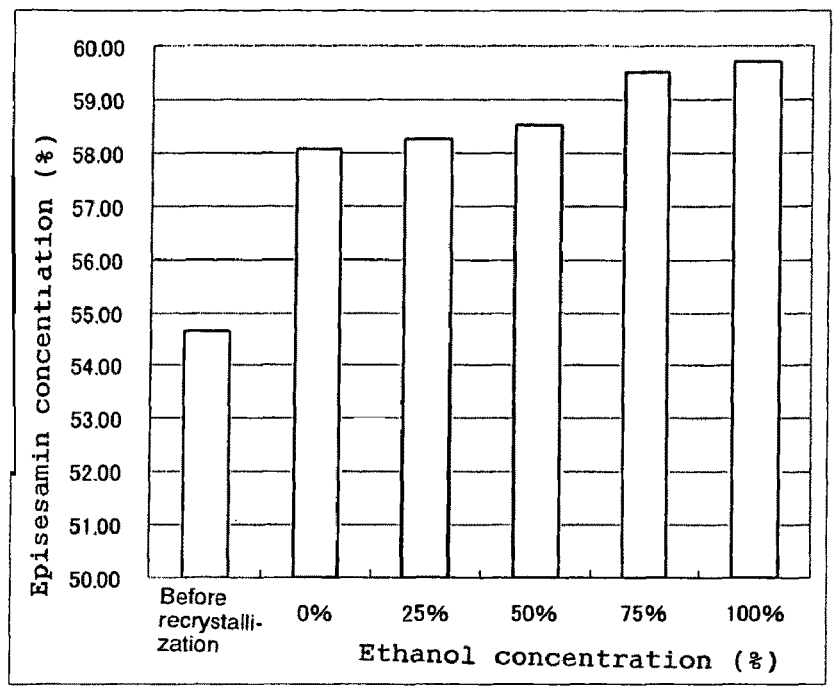
[FIG. 4]
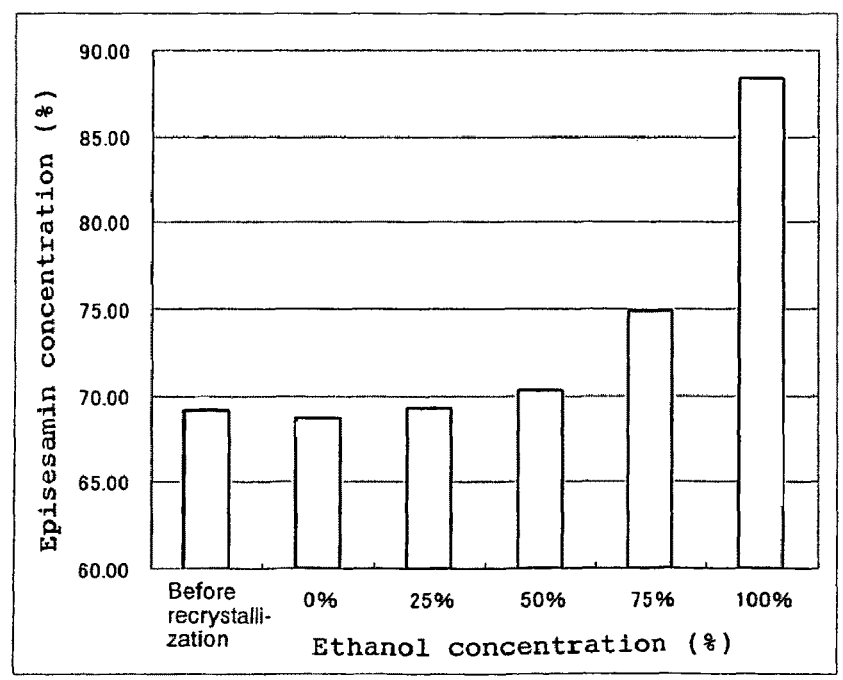

[FIG. 5]
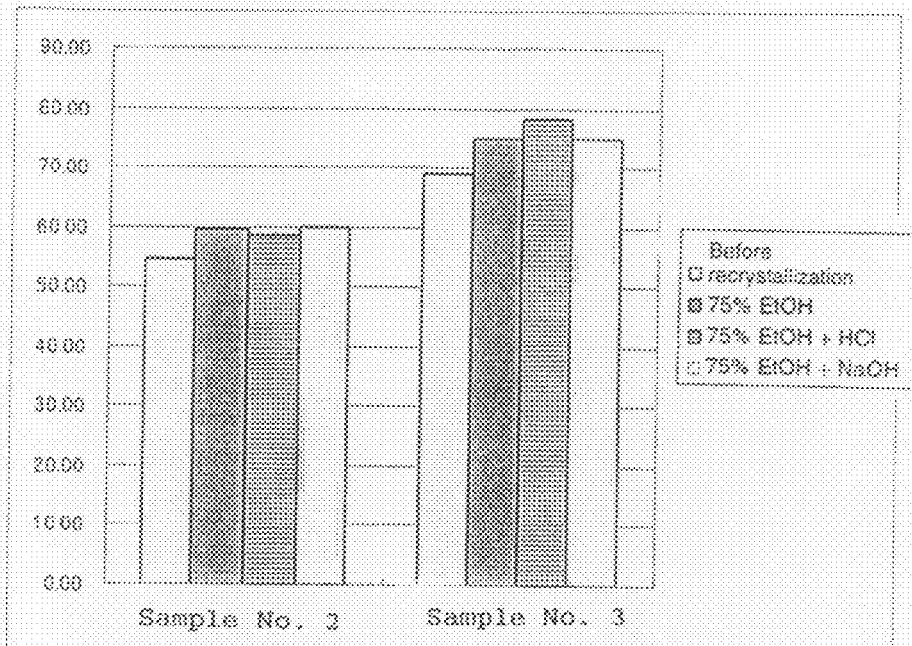
[FIG. 6]
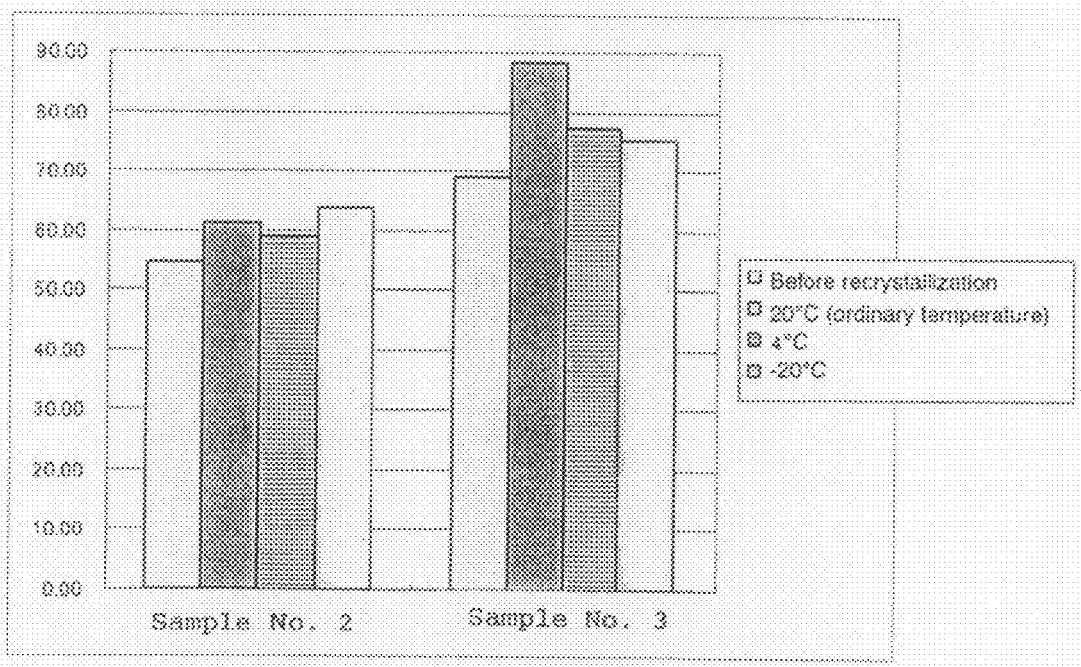

METHOD OF REFINING EPISESAMIN

CROSS REFERENCE TO RELATED APPLICATIONS

This application is the National Stage of International Application No. PCT/JP2006/321828, filed Nov. 1, 2006, and claims benefit of Japanese Application No. 2005-324045, filed Nov. 8, 2005, both of which are herein incorporated by reference in their entirety.

TECHNICAL FIELD

This invention relates to a method of refining episesamin from a mixture of sesamin components.

BACKGROUND ART

Various kinds of sesame lignan are found in sesame seeds and it is known that they usually contain not only sesamin in about 0.1-0.5 wt % but also sesamol, sesamolin, sesaminol and the like. Unrefined sesame oil expressed from sesame seeds contain about 0.5-1.0 wt % of sesamin as a sesame lignan.

It is also known that when sesame seeds are treated with mineral acids such as sulfuric acid, activated clay, or the like, sesamin components are formed, including not only sesamin but also episesamin that is an optically converted product of sesamin and which inherently is not present in sesame seeds (non-patent reference 1 and non-patent reference 2). Such sesame lignans mainly comprising sesamin components are known to have various physiological activities including, for example, the action of inhibiting Δ5-unsaturation enzymes, anti-oxidizing action against lipids, antihypertensive action, the action of improving hepatic functions, the action of scavenging active oxygen, cholesterol lowering action, and the action of preventing sickness from drinking and, hence, they are expected to prove useful as health food.

As a method by which products containing sesamin components at high concentrations can be separated from sesame seeds, it has been proposed to press sesame seeds, subject the pressed seeds to extraction with an organic solvent, and perform molecular distillation on the extract. Specific examples include: (1) distilling sesame oil with steam under reduced pressure and subjecting the distillate to molecular distillation (see patent reference 1); (2) distilling sesame oil with steam under reduced pressure, performing esterification reaction and/or ester exchange reaction on the distillate, and subjecting the reaction product to molecular distillation (see patent reference 2); (3) distilling sesame oil with steam, mixing the distillate with an aqueous solvent, and performing crystallization in the mixed system in the presence of an alkali (see patent reference 3); (4) distilling sesame oil with steam under reduced pressure, mixing the distillate with an aqueous ethanol solution containing at least 40 wt % of ethanol, separating the solution fraction from the mixed system, and adding an alkali to the solution fraction for crystallization (see patent reference 3); (5) distilling sesame oil with steam under reduced pressure, mixing the distillate with an aqueous ethanol solution containing at least 40 wt % of ethanol, separating the solution fraction from the mixed system, performing adsorption treatment on the separated solution fraction with an adsorbent, and performing desorption/elution from the adsorbent (see patent reference 4); and the like. It has also been disclosed that the molecular distillation, crystallization or desorption/elution that are performed in (1)-(5) above may even be followed by recrystallization treatment to increase the concentrations of sesamin components (wherein the term "sesamin components" is defined to comprise sesamin, episesamin and sesamolin) (patent references 1-2).

Recent studies on the differences between the physiological activities of sesamin and episesamin have revealed the superiority of episesamin over sesamin, as exemplified by higher transfer into organs, enhanced gene expression of β-oxidation enzymes in the liver, and marked enhancement of enzymatic activity (non-patent reference 3 and non-patent reference 4).

[Patent reference 1] the official gazette of JP 7-25764 B
[Patent reference 2] the official gazette of JP 2003-183172 A
[Patent reference 3] the official gazette of JP 10-7676 A
[Patent reference 4] the official gazette of JP 6-89353 B
[Non-patent reference 1] Namiki et al., "Goma—Sono Kagaku to Kinousei (Sesame—Its Science and Functions)", Maruzen Planet Co., Ltd. (1998)
[Non-patent reference 2] Fukuda, Y. et al., J. Am. Oil Chem. Soc., 63, 1027-1031 (1986)
[Non-patent reference 3] Sawada, R. et al., Lipids, 34, 633 (1999)
[Non-patent reference 4] Kushiro, M. et al., J. Nutr. Biochem., 13, 289-295 (2002)

DISCLOSURE OF THE INVENTION

Problems to be Solved by the Invention

As described above, various methods have been proposed as techniques by which products containing sesamin components at high concentrations can be separated from sesame oil; however, in order to refine episesamin from a mixture of sesamin components, in particular, a mixture containing sesamin and episesamin, there have been available very few methods including isolation by column chromatography, but such methods involve complicated operations and, what is more, they yield such small quantities of the composition at a time that they feature only low efficiency. An object of the present invention is to provide a method by which episesamin having high in vivo activity can be efficiently refined from the mixture of sesamin components.

Means for Solving the Problems

As a result of intensive studies made in order to attain the above-stated object, the present inventors found that the sesamin components, i.e., sesamin, episesamin and diasesamin, had different solubilities in aqueous media, namely, water, water-soluble media, or aqueous solutions of such media. Then, the present inventors brought into contact with the aqueous medium a mixture of sesamin components that was in a solid state or at least part of which was in a dissolved state, thereby forming a slurried mixture, and thereafter separated the solids from the mixture to yield an episesamin-enriched composition with an increased relative episesamin content. Specifically, the mixture of sesamin components containing sesamin, episesamin and diasesamin was dissolved in the aqueous medium under heating and thereafter the solution was slowly cooled to recrystallize, thereby enabling the production of an episesamin-enriched composition with an increased relative episesamin content. The present inventors further found that when the concentration of episesamin in the mixture of sesamin components before recrystallization was greater than about 50 wt %, in particular, at 64 wt % and above, the episesamin's relative content in the crystal formed by recrystallization was remarkably increased; this finding has led to the completion of the present invention.

Thus, the present invention relates to the following methods of refining episesamin.

1. A method of refining episesamin which comprises bringing into contact with an aqueous medium a mixture of sesamin components that is in a solid state or at least part of which is in a dissolved state, thereby forming a slurried mixture, and thereafter separating the solids from the mixture or performing recrystallization with an aqueous medium, thereby yielding an episesamin-enriched composition with an increased relative episesamin content.
2. The method of refining episesamin as described in 1 above, wherein the mixture of sesamin components to be refined is a mixture of sesamin components which contains at least sesamin and episesamin.
3. The method of refining episesamin as described in 2 above, wherein the episesamin-enriched composition has a concentration of episesamin greater than 55 wt %, preferably at least 70 wt %, based on the total weight of sesamin and episesamin.
4. The method of refining episesamin as described in any one of 1-3 above, wherein the aqueous medium is water, a water-soluble medium or an aqueous solution of a water-soluble medium.
5. The method of refining episesamin as described in 4 above, wherein the aqueous medium is water, an alcohol, or an aqueous alcohol solution.
6. The method of refining episesamin as described in 5 above, wherein the aqueous medium is ethanol or an aqueous ethanol solution.
7. The method of refining episesamin as described in any one of 1-6 above, including recrystallizing the mixture of sesamin components with the aqueous medium to yield the episesamin-enriched composition.
8. The method of refining episesamin as described in any one of 1-7 above, wherein the mixture of sesamin components with an enhanced episesamin concentration has been produced by the following steps:
(1) dissolving the mixture of sesamin components in an oil or fat under heating; and
(2) selectively crystallizing episesamin by means of a recrystallization technique so as to yield an episesamin-containing composition with an enhanced episesamin concentration.
9. The method of refining episesamin as described in 8 above, wherein the episesamin content in the mixture of sesamin components is at least 64 wt %.
10. The method of refining episesamin as described in 8 or 9 above, wherein the oil or fat having the mixture of sesamin components dissolved therein is subjected to acidic catalyst treatment.
11. The method of refining episesamin as described in any one of 1-7 above, wherein the mixture of sesamin components with an enhanced episesamin concentration has been produced by the following steps:
(1) performing molecular distillation on a mixture containing sesamin components that has been refined from sesame oil, thereby giving a fraction in which the sesamin components are enriched; and
(2) dissolving the fraction in water, a water-soluble solvent or a mixture thereof, optionally adding an alkali, and then precipitating the sesamin components to yield a sesamin/episesamin mixture with an enhanced episesamin concentration.
12. The method of refining episesamin as described in 11 above, wherein the episesamin-enriched composition has a concentration of episesamin greater than 55 wt %, preferably at least 70 wt %, based on the total weight of sesamin and episesamin.

Effects of the Invention

According to the method of the present invention for refining episesamin, a mixture of sesamin components similar in structure, namely, a mixture of episesamin and at least one component selected from sesamin and diasesamin can be treated to yield an episesamin-enriched composition with an enhanced relative episesamin content, specifically one containing episesamin at a concentration greater than 55 wt %.

BRIEF DESCRIPTION OF THE DRAWINGS

FIG. 1 is an HPLC chart for the samples of Examples.
FIG. 2 is a graph showing how the episesamin concentration (wt %) that accounted for the mixture of sesamin components varied in the samples of Examples before and after recrystallization. The mixture having an episesamin concentration before recrystallization as plotted on the horizontal axis was recrystallized to provide a final episesamin concentration (as plotted on the vertical axis).
FIG. 3 is a graph showing how the episesamin concentration (wt %) that accounted for the mixture of sesamin components varied when recrystallization was performed with water, ethanol or an aqueous ethanol solution (ethanol v/v) being used as an aqueous medium.
FIG. 4 is a graph showing how the episesamin concentration (wt %) that accounted for the mixture of sesamin components varied when recrystallization was performed with water, ethanol or an aqueous ethanol solution (ethanol v/v) being used as an aqueous medium.
FIG. 5 is a graph showing how the episesamin concentration (wt %) that accounted for the mixture of sesamin components varied when recrystallization was performed with an aqueous ethanol solution (ethanol v/v), an aqueous ethanol solution+HCl (1 N) or an aqueous ethanol solution+NaOH (1 N) being used as an aqueous medium.
FIG. 6 is a graph showing how the episesamin concentration (wt %) that accounted for the mixture of sesamin components varied when cooling during recrystallization was performed at 20° C., 4° C. or −20° C.

BEST MODES FOR CARRYING OUT THE INVENTION

Mixture of Sesamin Components

As used herein, the mixture of sesamin components means episesamin containing lignan compounds or an extract mainly comprising such lignan compounds. The mixture of sesamin components to be refined usually contains not only episesamin but also lignan compounds such as sesamin and diasesamin, as well as impurities such as water.

The refining method of the present invention may be applied to the mixtures of sesamin components that are prepared by conventional known methods. Examples include: the method as described in the official gazette of Japanese Patent No. 3001589, which comprises adding an organic solvent to sesame oil treated with activated clay, leaving the mixture to stand still, then separating off the filtrate or the overlying liquid, and distilling off the organic solvent to yield lignan compounds (a mixture of sesamin components); the method as described in the official gazette of Japanese Patent No. 3205315, which comprises adding an aqueous ethanol solution to scum as a by-product to the process of sesame oil production (the distillate from the deodorizing step), leaving the mixture to stand still overnight so that the solvent soluble fraction separates off in layer, and precipitating lignan compounds (a mixture of sesamin components) in the presence of an alkali; the method as described in the official gazette of JP 2003-192562 A, which comprises deoxidizing sesame oil extracted from sesame seeds by pressing, then deodorizing and discoloring the deoxidized sesame oil with activated clay, distilling the thus treated sesame oil with steam under reduced pressure, mixing the distillate with an aqueous solvent, and performing precipitation in the mixed system in the presence of an alkali so as to yield a composition containing sesamin components at high concentrations; the composition containing sesamin components at high concentrations may optionally be dissolved in ethanol and subjected to recrystallization to yield a mixture of sesamin components; while any of these methods may be employed, the present invention is by no means limited to the mixtures of sesamin components that are prepared by those methods.

The present inventors have already found that episesamin can be selectively crystallized by dissolving the sesamin-containing composition in MCT (medium-chain fatty acid triglyceride), then treating the solution with an acid catalyst such as activated clay, and adding episesamin seed crystals to the filtrate (PCT/JP 2006/319493). The refining method of the present invention can of course be applied to this product of recrystallization from MCT which is obtained by selective crystallization of episesamin.

(Refining Method)

The present invention starts with bringing the mixture of sesamin components to be refined into contact with an aqueous medium. After bringing the mixture of sesamin components into contact with an aqueous medium, episesamin can be refined by 1) a contact technique or 2) a recrystallization technique.

(Aqueous Medium)

The aqueous medium to be contacted in 1) or 2) above may be any medium that dissolves sesamin and episesamin by different degrees and may be exemplified by water; alcoholic solvents such as methanol, ethanol, and propanol; acetone; ethyl acetate; ether-containing solvents such as diethyl ether; and aqueous solutions thereof. One or more of these mediums may be used but ethanol is preferably used for various reasons such as low toxicity, a relatively low enough boiling point to permit easy removal after extraction, and easy availability. If ethanol or an aqueous ethanol solution is used as a solvent, they may remain in the episesamin-enriched composition without doing any harm to humans and, hence, the refined episesamin-enriched composition can advantageously be used as a composition for food.

If an aqueous ethanol solution is used as a solvent, in order to increase the extraction efficiency and reduce the proportion of impurities, namely, to increase the purity of the resulting episesamin-enriched composition (its episesamin concentration), it is preferred to use an aqueous ethanol solution of high ethanol concentration, specifically, an aqueous ethanol solution containing at least 75 v %, more preferably at least 90 v %, of ethanol.

(Contact Technique)

In the contact technique of above 1), the mixture of sesamin components to be refined is brought into contact with the aqueous medium to form a slurried mixture in which the mixture of sesamin components is partly in a dissolved state and thereafter the solids are separated from the mixture. Episesamin has a slightly different solubility in the aqueous medium from other components or impurities (e.g. sesamin, diasesamin, etc.) and episesamin tends to be less soluble. Therefore, when the mixture of sesamin components is brought into contact with the aqueous medium, substances other than episesamin become partly in a dissolved state. The amount of the aqueous medium to be used is not limited to any particular value; however, if its quantity is too small, the impurities will dissolve only insufficiently and if it is too much, separation of the solids will become inefficient. The usual quantity is 5-100 times the weight of the mixture of sesamin components to be refined. The temperature of contact is usually on the order of 0-70° C., preferably 10-50° C., and more preferably 20-40° C. The method of effecting contact is not limited in any particular way and examples include: a method in which the mixture of sesamin components and the aqueous medium are charged into a vessel, where they are left to stand to have mutual contact; a method in which the two materials are brought into mutual contact in a vessel equipped with an agitator; and a method in which they are brought into mutual contact in a solid-liquid extractor. If desired, multiple units of these apparatus may be used so that the mixture of sesamin components is allowed to have multiple contacts in two or more stages.

The next step in the present invention consists of separating the solids from the slurried mixture obtained by bringing the mixture of sesamin components into contact with the aqueous medium. The method of separating the solids is not limited in any particular way and conventionally used solid-liquid separators such as a filter and a centrifuge may be employed. The separated and recovered solids are dried to give a mixture of sesamin components with an enhanced relative episesamin content.

(Recrystallization Technique)

Episesamin refining by the recrystallization technique of 2) above can efficiently enhance the purity of episesamin as compared with the contact technique of 1) above. The recrystallization technique starts with dissolving the mixture of sesamin components to be refined in the aqueous medium under heating. The amount of the aqueous medium to be used to dissolve the mixture of sesamin components can be set at any desired value and depending on the contents of non-episesamin ingredients or impurities in the mixture of sesamin components, its quantity is generally about 5-100 times the amount (by weight ratio) of the mixture of sesamin components. If the quantity of the aqueous medium is too small, it takes an unduly long time to dissolve all sesamin components or it sometimes occurs that not all sesamin components will dissolve. On the other hand, if the quantity of the aqueous medium is too large, episesamin will be recrystallized in a lower yield.

The heating temperature for dissolving the mixture of sesamin components is the one at which all sesamin components will dissolve. This temperature, which varies with the purity of the mixture of sesamin components as well as with the type and quantity of the solvent to be used to dissolve it, is preferably not higher than the boiling point of the solvent (100.0° C. if it is water and 78.3° C. in the case of ethanol). This, however, is not limiting if a reflux pipe is used and in the case of using a reflux pipe with ethanol as the aqueous medium, heating may be done up to about 80-90° C. Starting from room temperature, the temperature is elevated up to an appropriate heating temperature so that the sesamin components are completely dissolved.

In the next step, the resulting solution is cooled to precipitate the episesamin crystal. Cooling is effected down to 50° C. or below, preferably down to 40° C. or below, thereby precipitating the episesamin crystal. If the cooling temperature is too low (specifically, if cooling is effected down to 4° C. or below), not only episesamin but also the sesamin crystal will precipitate and the purity of episesamin in the crystal obtained by recrystallization may sometimes drop; to avoid this problem, it is recommended to cool the solution to the lowest possible temperature zone where only the episesamin crystal can be precipitated.

Subsequently, the slurry containing the thus obtained episesamin crystal is separated into the episesamin crystal and the mother liquor. For this separation, conventionally used solid-liquid separators such as a filter and a centrifuge may be employed. In this case, depending on the need, the episesamin crystal may be washed with an aqueous medium, preferably an alcohol, more preferably ethanol.

The mother liquor separated off contains sesamin, so it is advantageously recovered for a second use as the material to be isomerized.

The separated episesamin crystal is then dried to yield a refined form of episesamin or episesamin-enriched composition. Drying is preferably performed under reduced pressure (ca. 1-100 mmHg) by heating at about 30-100° C., preferably at about 40-80° C.

This recrystallizing procedure helps remove the non-episesamin ingredients and impurities in the mixture of sesamin components, so that sesamin and/or diasesamin having a similar structure to episesamin can be removed or reduced in content. As a result, the episesamin crystal (episesamin-enriched composition) contains episesamin in a concentration exceeding 55 wt %, preferably 70 wt % or more based on the total weight of sesamin and episesamin. Note that if the mixture of sesamin components to be refined contains very large amounts of non-episesamin ingredients or impurities, the recrystallizing procedure described above may be repeated as many times as are necessary to reduce the content of the impurities.

(Sesamin/Episesamin Mixture with Enhanced Episesamin Concentration)

If a sesamin/episesamin mixture with an enhanced episesamin concentration, specifically, a sesamin/episesamin mixture containing at least 64 wt % of episesamin is used as the mixture of sesamin components to be refined, episesamin in the episesamin crystal (episesamin-enriched composition) obtained by the above-described recrystallizing procedure can be enhanced remarkably, thus leading to an improvement in the refining efficiency of episesamin. While the sesamin/episesamin mixture with an enhanced episesamin concentration that can be used may be of any type, a specific example is a sesamin/episesamin mixture with an enhanced episesamin concentration that has been produced by the following steps:
(1) heating the mixture of sesamin components in an oil or fat under heating; and
(2) selectively crystallizing episesamin by means of a recrystallization technique so as to yield an episesamin-containing composition with an enhanced episesamin concentration.

Here, the oil or fat is preferably chosen from among oils or fats that can dissolve sesamin and episesamin by different degrees and MCT can advantageously be used. If the oil or fat that have the sesamin/episesamin mixture dissolved therein is subjected to treatment with an acidic catalyst (such as activated clay), one can obtain the sesamin/episesamin mixture with an enhanced episesamin concentration.

EXAMPLES

The refining method of the present invention is described below in detail by reference to examples, which are by no means intended to limit the present invention.

Example 1

Preparation of Samples

The eight samples shown in the following Table 1 were prepared. All percentages in Table 1 as well as in Tables 2 and 3 to be set forth later are on a weight basis.

TABLE 1

| Sample No. | 1 | 2 | 3 | 4 | 5 | 6 | 7 | 8 |
|---|---|---|---|---|---|---|---|---|
| Sesamin (%) | 50.57 | 42.12 | 28.20 | 22.44 | 7.87 | 1.86 | 31.4 | 32.0 |
| Episesamin (%) | 48.21 | 54.65 | 69.18 | 75.40 | 89.35 | 95.72 | 64.4 | 66.8 |

As sample Nos. 1 and 2, there were used the sesamin and episesamin mixtures (sesamin/episesamin mixtures) purified in accordance with the method described in the official gazette of JP 10-7676 A. As sample Nos. 3-8, there were prepared and used sesamin/episesamin mixtures that were enhanced in episesamin concentration by the following method: 2.8 g of a sesamin-episesamin mixture (sesamin: 99.1 wt %; episesamin: 0.9 wt %) was mixed with 20 g of an oil or fat (MCT; RIKEN VITAMIN CO., LTD., trade name "ACTOR M-1") and heated at 120° C. under agitation until the mixture was completely dissolved. To the solution, 0.4 g of activated clay (MIZUSAWA INDUSTRIAL CHEMICALS, LTD., trade name "GALLEON EARTH V2R") was added and the mixture was stirred at 120° C. for a continuous period of 30 minutes, then followed by filtration to remove the waste clay. The filtrate was recovered and slowly cooled; when the liquid's temperature reached 60° C., 2.8 mg of episesamin (100% pure) was added as seed crystals and crystallization was performed. By adjusting the crystallization period between 30 minutes and overnight, samples (sample Nos. 3-8) having different concentrations of episesamin in the sesamin/episesamin mixtures were prepared. The resulting slurry was subjected to solid-liquid separation by suction filtration, yielding the episesamin-containing products to be used in the following experiments.

Example 2

Ethanol Crystallization Technique—1

A hundred grams of a 99.5 v % aqueous ethanol solution was weighed in an eggplant type flask of 200 ml in capacity; the flask was then charged with 5.0 g each of sample Nos. 1-8 prepared in Example 1; thereafter, the flask was equipped with a reflux pipe and the mixture was heated in an oil bath at 90° C. under agitation for 15 minutes until the mixture was dissolved. The solution was left to stand still overnight at 20° C. so as to precipitate the episesamin crystal (episesamin-enriched composition). The precipitating crystal was separated by suction filtration and dried at 70° C. for 60 minutes. The resulting crystal was finely pulverized in a mortar and a portion of the powder was taken as a sample for HPLC analysis. The thus obtained sample was subjected to HPLC under the following conditions to analyze the composition of sesamin/episesamin.

(HPLC Conditions)
Column: Inertsil ODS-3 (product of GL-SCIENCE) 4.6×150 mm;
Column temperature: 40° C.
Mobile phase: methyl alcohol/water=7:3
Flow rate: 1 ml/min
Detector: UV 290 nm The results of analysis by HPLC are shown in Table 2, and HPLC charts for sample Nos. 2 and 3 are shown in FIG. 1. As is clear from Table 2 and FIG. 1, the compositions after recrystallization had higher episesamin concentrations than the mixtures of sesamin components before recrystallization. It was thus suggested that episesamin was refined from the sesamin and episesamin mixture by recrystallization with ethanol. In addition, almost all impurities (including diasesamin) that were not sesamin or episesamin could be removed.

TABLE 2

|  | Sample No. | 1 | 2 | 3 | 4 | 5 | 6 | 7 | 8 |
|---|---|---|---|---|---|---|---|---|---|
| Before recrystallization | Sesamin (%) | 50.57 | 42.12 | 28.20 | 22.44 | 7.87 | 1.86 | 31.4 | 32.0 |
| | Episesamin (%) | 48.21 | 54.65 | 69.18 | 75.40 | 89.35 | 95.72 | 64.4 | 66.8 |
| After recrystallization | Sesamin (%) | 46.94 | 35.32 | 8.1 | 1.89 | 0.64 | 0.05 | 24.2 | 13.0 |
| | Episesamin (%) | 52.36 | 63.37 | 90.78 | 96.58 | 97.87 | 98.8 | 75.5 | 86.7 |

Example 3

Ethanol Crystallization Technique—2

Using the episesamin crystal (episesamin-enriched composition) of sample No. 2 (sesamin: 35.32 wt %; episesamin: wt %) or the episesamin crystal (episesamin-enriched composition) of sample No. 7 (sesamin: 0.05 wt %; episesamin: wt %), both obtained in Example 2, recrystallization was performed in ethanol as in Example 2 to precipitate the episesamin crystal (episesamin-enriched composition) and the thus obtained crystal was subjected to HPLC analysis as in Example 2.

The results are shown in Table 3. It was confirmed that by repeating the recrystallization process, the concentration of episesamin was enhanced.

TABLE 3

| | Sample No. | 2 | 6 |
|---|---|---|---|
| Before recrystallization | Sesamin (%) | 42.12 | 1.86 |
| | Episesamin (%) | 54.65 | 95.72 |
| After recrystallization | Sesamin (%) | 35.32 | 0.05 |
| | Episesamin (%) | 63.37 | 98.8 |
| After recrystallization (second time) | Sesamin (%) | 30.97 | 0.03 |
| | Episesamin (%) | 68.09 | 99.24 |

From the results of Examples 2 and 3, the profiles of episesamin concentration both before and after recrystallization were plotted (FIG. 2). When the mixture of sesamin components before recrystallization was an episesamin-enriched mixture of sesamin components with an episesamin content of 64 wt % or more, the resulting episesamin crystal (episesamin-enriched composition) had a markedly enhanced episesamin concentration, thus suggesting its high efficiency as the episesamin refining method.

Example 4

Water/Ethanol Crystallization Technique—1

As aqueous media, the following five types were used, with water:ethanol (weight ratio) being at 100:0, 75:25, 50:50, 25:75, and 0:100 (a 99.5 v % aqueous ethanol solution was used as ethanol). Fifty grams of one of these aqueous media was weighed in an eggplant type flask of 100 ml in capacity; the flask was then charged with 2.5 g of sample No. 2 (sesamin: 42.12 wt %; episesamin: 54.65 wt %) prepared in Example 1; thereafter, the flask was equipped with a reflux pipe and the mixture was heated in an oil bath at 90° C. under agitation for 15 minutes until the mixture was dissolved. The solution was left to stand still overnight at 20° C. so as to precipitate the episesamin crystal (episesamin-enriched composition), which was subjected to HPLC analysis as in Example 2.

The results are shown in FIG. 3. It was suggested that the higher the ethanol concentration, the higher the episesamin concentration.

Example 5

Water/Ethanol Crystallization Method—2

Using sample No. 3 (sesamin: 28.2 wt %; episesamin: 69.18 wt %) prepared in Example 1, namely, the mixture of sesamin components with an enhanced ethanol concentration, recrystallization was performed as in Example 4 to precipitate the episesamin crystal (episesamin-enriched composition) and the thus obtained crystal was subjected to HPLC analysis as in Example 2.

The results are shown in Table 4. As in Example 4 (FIG. 3), it was suggested that the higher the ethanol concentration, the higher the concentration of episesamin in the sesamin/episesamin mixtures that was obtained by recrystallization; however, it was also suggested that without using an aqueous ethanol solution containing more than 50 v % of ethanol, episesamin could not be selectively crystallized from the mixture of sesamin components before recrystallization, namely, episesamin could not be refined. It was also confirmed that the episesamin concentration was remarkably enhanced by using ethanol (100% pure). The amounts (g) of the episesamin crystal obtained were 2.38 g, 2.37 g, 2.21 g, 2.07 g, and 1.63 g for water:ethanol ratios of 100:0, 75:25, 50:50, 25:75, and 0:100, respectively.

Example 6

Ethanol Precipitation Technique—the Effect of pH

As aqueous media, the following three types were used, the first being a 75 v % aqueous ethanol solution (75% EtOH), the second being one to which 4 N HCl was added to give 75% EtOH (75% EtOH+HCl), and the last being one to which 4 N NaOH was added to give 75% EtOH (75% EtOH+NaOH). Fifty grams of one of these aqueous media was weighed in an eggplant type flask of 100 ml in capacity; the flask was then charged with 2.5 g of sample No. 2 (sesamin: 42.12 wt %; episesamin: 54.65 wt %) or sample No. 3 (sesamin: 28.2 wt %; episesamin: 69.18 wt %), both prepared in Example 1; thereafter, the flask was equipped with a reflux pipe and the mixture was heated in an oil bath at 90° C. under agitation for 15 minutes until the mixture was dissolved. The solution was left to stand still overnight at 20° C. so as to precipitate the episesamin crystal (episesamin-enriched composition), which was then subjected to HPLC analysis as in Example 2.

The results are shown in FIG. 5. It was suggested that episesamin was refined by crystallization in the aqueous ethanol solution but the addition of 1 N HCl or 1 N NaOH was found to have no effect on the episesamin concentration.

Example 7

Ethanol Precipitation Technique—the Effect of Cooling Temperature

Fifty grams of a 99.5 v % aqueous ethanol solution was weighed in an eggplant type flask of 100 ml in capacity; the flask was then charged with 2.5 g of sample No. 2 (sesamin: 42.12 wt %; episesamin: 54.65 wt %) or sample No. 3 (sesamin: 28.2 wt %; episesamin: 69.18 wt %), both prepared in Example 1; thereafter, the flask was equipped with a reflux pipe and the mixture was heated in an oil bath at 90° C. under agitation for 15 minutes until the mixture was dissolved. The solution was left to stand still for 4 hours under different temperature conditions (20° C., 4° C., and −20° C.) so as to precipitate the episesamin crystal (episesamin-enriched composition). The obtained episesamin crystal was then subjected to HPLC analysis as in Example 2.

The results are shown in FIG. 6. When sample No. 2 was used, the concentration of episesamin in the episesamin crystal obtained by recrystallization was not dependent on the cooling temperature; however, when sample No. 3 (a mixture of sesamin components with an enhanced episesamin concentration) was used, the concentration of episesamin in the episesamin crystal was decreased in the order of 20° C.>>4° C.>−20° C., thus suggesting that recrystallization should preferably be performed at about 20° C. The amounts (g) of the episesamin crystal obtained were 1.63 g, 1.92 g, and 2.01 g for 20° C., 4° C., and −20° C., respectively.

INDUSTRIAL APPLICABILITY

In order to refine episesamin having high in vivo activity from a mixture of sesamin components, in particular, a mixture containing sesamin and episesamin, there have been available very few methods, such as column chromatography, that not only involve complicated operations but which also yield such small quantities of the composition at a time that they feature only low efficiency. In accordance with the episesamin refining method of the present invention, episesamin-enriched compositions having high relative episesamin content can be obtained by a simple procedure in high efficiency, so inexpensive and high-volume use of episesamin-enriched compositions has become possible.

The invention claimed is:

1. A method of refining episesamin comprising recrystallizing a mixture of sesamin components with an aqueous medium to yield an episesamin-enriched composition with an increased relative episesamin content, wherein the mixture of sesamin components has an episesamin content of at least 64 wt %.

2. The method of refining episesamin according to claim 1, wherein the mixture of sesamin components contains at least sesamin and episesamin.

3. The method of refining episesamin according to claim 2, wherein the episesamin-enriched composition has a concentration of episesamin at least 70 wt %, based on the total weight of sesamin and episesamin.

4. The method of refining episesamin according to claim 1, wherein the aqueous medium is water, a water-soluble medium or an aqueous solution of a water-soluble medium.

5. The method of refining episesamin according to claim 4, wherein the aqueous medium is water, an alcohol, or an aqueous alcohol solution.

6. The method of refining episesamin according to claim 5, wherein the aqueous medium is ethanol or an aqueous ethanol solution.

7. A method of refining episesamin comprising the following steps:
(1) dissolving a mixture of sesamin components in an oil or fat under heating;
(2) selectively crystallizing episesamin by means of a recrystallization technique to yield a mixture of sesamin components having an episesamin content of at least 64 wt %; and
(3) recrystallizing the mixture of sesamin components of the step (2) with an aqueous medium to yield an episesamin-enriched composition.

8. The method of refining episesamin according to claim 7, wherein the oil or fat having the mixture of sesamin components dissolved therein is subjected to acidic catalyst treatment.

9. A method of refining episesamin comprising the following steps:
(1) performing molecular distillation on a mixture containing sesamin components that has been refined from sesame oil, thereby giving a fraction in which the sesamin components are enriched;
(2) dissolving the fraction in water, a water-soluble solvent or a mixture thereof, and then precipitating the sesamin components to yield a mixture of sesamin components having an episesamin content of at least 64 wt %; and
(3) recrystallizing the mixture of sesamin components of the step (2) with an aqueous medium to yield an episesamin-enriched composition.

10. The method of refining episesamin according to claim 9, wherein the episesamin-enriched composition has a concentration of episesamin-at least 70 wt %, based on the total weight of sesamin and episesamin.

11. The method of refining episesamin according to claim 9, wherein the step (2) further comprises adding an alkali.

12. A method of refining episesamin comprising recrystallizing a mixture of sesamin components with an aqueous medium in the absence of an alkali to yield an episesamin-enriched composition with an increased relative episesamin content, wherein the mixture of sesamin components has an episesamin content of at least 64 wt %.

* * * * *